United States Patent [19]

Derbyshire

[11] Patent Number: 5,007,926

[45] Date of Patent: Apr. 16, 1991

[54] EXPANDABLE TRANSLUMINALLY IMPLANTABLE TUBULAR PROSTHESIS

[75] Inventor: Garrett Derbyshire, Philadelphia, Pa.

[73] Assignee: The Trustees of the University of Pennsylvania, Philadelphia, Pa.

[21] Appl. No.: 315,465

[22] Filed: Feb. 24, 1989

[51] Int. Cl.$^5$ .............................................. A61F 2/06
[52] U.S. Cl. ......................................... 623/1; 623/12; 606/191; 606/194
[58] Field of Search ............... 623/1, 11, 12; 606/151, 606/153, 155, 191, 194, 198

[56] References Cited

U.S. PATENT DOCUMENTS

| | | | |
|---|---|---|---|
| 4,204,282 | 5/1980 | Bolt | 623/11 X |
| 4,733,665 | 3/1988 | Palmaz | 623/1 X |
| 4,740,207 | 4/1988 | Kreamer | 623/12 X |
| 4,854,316 | 8/1989 | Davis | 606/153 |
| 4,856,516 | 8/1989 | Hillstead | 606/194 |
| 4,877,030 | 10/1989 | Beck et al. | 623/1 X |

Primary Examiner—Randall L. Green
Assistant Examiner—Stephanie L. Iantorno
Attorney, Agent, or Firm—Woodcock Washburn Kurtz Mackiewicz & Norris

[57] ABSTRACT

Improved expandable tubular prostheses and methods for their use are provided by this invention. The prostheses include a resilient member having longitudinal sides and transverse ends and are disposed in a tubular configuration about a transverse axis. The resilient member comprises ratcheting means for allowing the selective radial expansion and locking of the tubular prostheses in at least one fixed diameter. The prosthesis can also be removed after temporary use.

7 Claims, 2 Drawing Sheets

EXPANDABLE TRANSLUMINALLY IMPLANTABLE TUBULAR PROSTHESIS

FIELD OF THE INVENTION

This invention relates to medical and surgical techniques for expanding body ducts which are difficult to access, and more particularly, to implantable stents for maintaining the patency of passages such as blood vessels, large airways, exocrine ducts, arterial aneurysms, urinary tracts and the like.

BACKGROUND OF THE INVENTION

In numerous medical and surgical techniques, there exists a need for inserting stents, implantable tubular prostheses, either temporarily or permanently, into various body ducts which are difficult to access. The stents may be used in cardiovascular medicine as an adjunct to percutaneous transcatheter angioplasty for treating ischemic heart disease and peripheral vascular disease or may be used in other medical or surgical applications to maintain the patency of passages. Transluminal stent implantation requires that the prosthesis diameter be smaller than the access passage during implantation. Following implantation, the stent would ideally restore the inside duct diameter to that of adjacent lumens in order to minimize turbulent flow.

The art has been replete with tubular prosthesis for generating a limited radial expansive force during surgical procedures.

U.S. Pat. No. 3,868,956 to Alfidi et al., Mar. 4, 1975, discloses an expandable device including a helical coil made of a nickel-titanium alloy with memory properties. Once placed in a desired position, the device is heated causing it to resume its expanded configuration. However, it is generally understood that the application of such heat may produce thermal tissue injury and inadvertently coagulate blood. Moreover, this device produces a limited expansive force and the small surface area of contact with the body duct leads to high localized stresses which may also damage tissue.

U.S. Pat. No. 4,503,569 to Dotter, Mar. 12, 1985, discloses a transluminally placed endovascular graft prosthesis including a helically wound coil having a generally tubular shape. This device is similar to that used by Alfidi et al. in that it relies on the shape memory of a metal alloy. Dotter seeks to reduce the risk of thermal tissue injury and blood coagulation by employing a lower restorative transition temperature material. However, this device also generates a limited radial expansive force which is also exerted over a generally small area resulting in high local stresses that lead to tissue injury.

U.S. Pat. No. 4,183,102 to Guiset, Jan. 15, 1980, discloses a prosthetic device for introduction into a lumen and for lining an interior wall portion of the lumen. This device includes a hollow toroidal inflatable sleeve which is expanded with pressurized fluid and can be placed in series to form an implantable sleeve. The sleeve generally has poor inside/outside diameter ratios which reduces fluid flow and causes turbulent flow in some instances. Moreover, this device is understood to be limited to short term applications.

U.S. Pat. No. 4,592,341 to Omagari et al., June 3, 1986, discloses methods and apparatus for guiding a prosthesis utilizing a flexible sheath in combination with a guide member. The prosthesis is not expandable and must be forcibly driven into the stricture. The rigid design may limit the usefulness of the device and has the capability of producing soft tissue trauma during insertion.

U.S. Pat. No. 4,655,771 to Wallsten, Apr. 7, 1987, discloses an expandable tubular prosthesis made of multiple helical coils wound in a braided configuration which are expanded radially by axially contracting the tube. This device, however, requires the prosthesis to be firmly fixed in position to remain expanded and generates only a limited radial expansive force.

U.S. Pat. No. 4,732,152 to Wallsten et al., Mar. 22, 1988, discloses an applicator used to place the expandable tubular prosthetic device described in the Wallsten '771 patent.

U.S. Pat. No. 4,665,918 to Garza et al., May 19, 1987, discloses a tubular prosthesis comprising a precompressed spring-like device wrapped around an applicator and held in a contracted state by a sheath. After proper device positioning in a blood vessel, the sheath is withdrawn and the precompressed spring radially expands by spring tension. However, this spring tension limits the maximum prosthetic diameter and the expansive force applied to the vessel walls.

While in the main, these devices are illustrative of the state of the art in transluminally expandable prostheses, there remains a need for improved prosthetic devices intended to be introduced, either temporarily or permanently, into the interior of longitudinal body passages and to be fixed in position to form a patent longitudinal channel. There also remains a need for implantable tubular prostheses which can avoid the need for surgical intervention by providing significant wall support and improved luminal patency while avoiding the many drawbacks of known radially expansive tubular prostheses.

SUMMARY OF THE INVENTION

This invention provides implantable tubular prostheses for insertion into body ducts and lumens which provide greater lateral force without attendant soft tissue trauma. The prostheses include a resilient member having longitudinal sides and transverse ends which is disposed in a generally tubular configuration about a transverse axis of the member. This resilient member further includes ratcheting means for permitting the selective radial expansion and locking of the tubular prosthesis in at least one fixed diameter, although multiple select diameters are also expressively provided.

Accordingly, an implantable tubular prosthesis or stent is provided by this invention which includes large surface area for reducing tissue injury caused by high localized stresses. The device may be expanded radially by known balloon catheter devices to generate greater expansive forces along the inner walls of body ducts such as blood vessels thereby permitting a larger dilation range than precompressed spring devices. Moreover, the ratchet locking design of these devices permits the prostheses to be radially expanded and locked at one or more selected diameters. Additionally, these devices can be made of bicompatible hypoallergenic materials such as polyfluorocarbon such as TEFLON brand polyfluorocarbon or stainless steel to permit temporary or permanent implantation.

It is therefore an object of this invention to provide implantable tubular prostheses exhibiting a ratcheting mechanism for selectively expanding and locking the tubular member against an inner wall of body ducts.

It is a further object of this invention to provide implantable tubular prostheses which can provide a relatively large surface area as well as a large dilation range when inserted into a body duct.

With these and other objects in view, which will become apparent to one skilled in the art as the description proceeds, this invention resides in the novel construction, combination, arrangement of parts and methods substantially as hereinafter described and more particularly defined by the attached claims.

BRIEF DESCRIPTION OF THE DRAWINGS

The accompanying drawings illustrate two embodiments of the invention according to the best mode so far known for the practical application of the principals thereof, and in which.

DETAILED DESCRIPTION OF THE INVENTION

The present invention provides implantable tubular prostheses and methods for their use. The implantable tubular prostheses of this invention include a resilient member having longitudinal sides and transverse ends. This resilient member is disposed in a generally tubular configuration about a transverse axis of the member. The resilient member further comprises ratcheting means for permitting the selective radial expansion and locking of the tubular prosthesis in at least one fixed diameter. As used herein, the term "ratcheting" refers to the ability of the implantable tubular prosthesis to expand radially in one direction and assume at least one fixed diameter, although multiple fixed diameters are contemplated. It is understood, however, that the prosthesis may be subsequently removed, e.g. using a balloon catheter to dilate the prosthesis and then applying endoscopic forceps to contract and remove it.

In more detailed embodiments of this prosthesis, the implant can include a flexible sheet of material having longitudinal sides and transverse ends, a first of said transverse ends comprising a free flap portion and a second of said transverse ends comprising a free flap catch portion. This flexible sheet includes a longitudinal groove disposed transversely across the flexible sheet between the free flap and free flap catch portions. The flexible sheet is disposed into a generally tubular configuration whereby the free flap is disposed within the longitudinal groove for fixing the diameter of the tubular prosthesis. Although not illustrated, multiple longitudinal grooves could be fabricated to permit multiple latching positions for achieving a variety of diameters.

In still a further embodiment of this invention another prosthesis embodiment is provided which includes a mesh member having individual longitudinal and transverse wires bound together and longitudinal sides and transverse ends, a first of the transverse ends having a projecting portion comprising individual wires of the mesh member. The mesh member is disposed in a generally tubular configuration whereby the individual wires of the projecting portion are disposed through the mesh member for fixing the diameter of the tubular prosthesis.

The novel method of this invention describes a procedure for implanting a tubular prosthesis into a body duct which comprises the step of providing a resilient member having longitudinal sides and transverse ends. This resilient member is disposed in a tubular configuration about a transverse axis of the member. The resilient member further comprises ratcheting means for permitting the selective expansion and locking of the tubular prosthesis in at least one fixed diameter. The method next includes disposing the tubular prosthesis transluminally within a body duct and then expanding the prosthesis against an inner wall of the duct before locking it into a fixed diameter for supporting the inner wall.

Figure 1A:
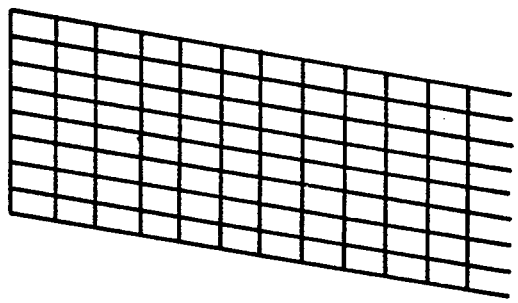
FIG. 1(a)-(e): describes a flexible mesh embodiment which can be fabricated into an implantable tubular prosthesis through simple bending of the end wire and curling of the mesh.
Figure 1B:
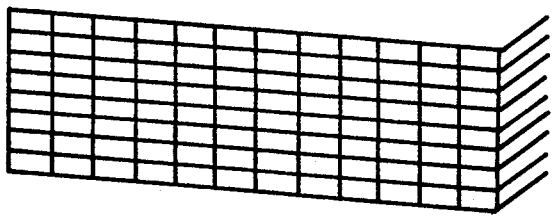
Figure 1C:
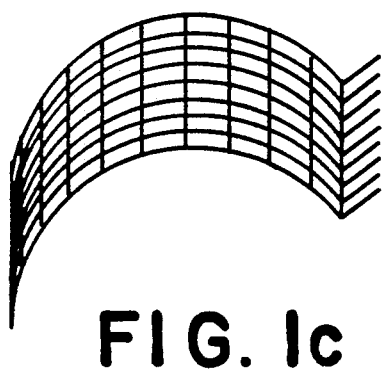
Figure 1D:
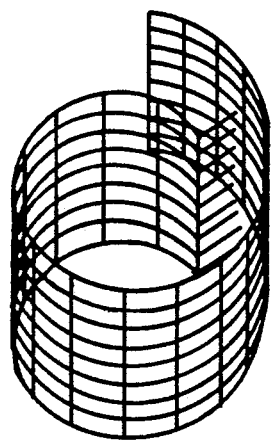
Figure 1E:
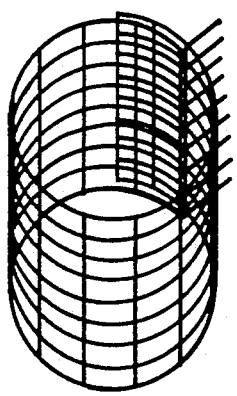

Referring now to the figures, and particularly FIG. 1(a)-(e) thereof, there is illustrated a preferred tubular prosthesis embodiment. FIG. 1(a) illustrates a plastic or metal mesh 10 used to form the flexible mesh embodiment of the tubular prosthesis. In this embodiment, the resilient member of the prosthesis is constructed using a flexible mesh 10 having a plurality of openings therein. The ratcheting means of this device comprises a projecting portion, preferably individual frayed wire-ends 20 of the flexible mesh 10 for engaging with a select number of the openings. Three edges of the mesh 10, two longitudinal and one transverse, are weaved into the flexible mesh 10 such that the individual wires are bound together. On the fourth edge, the other transverse end of the prosthesis, the frayed wire-ends are angled as illustrated in FIG. 1(b) for enabling an engagement with the select number of openings of the flexible mesh 10. The flexible mesh 10 is preferably rolled as described in FIG. 1(c)-(d), to reduce the radial dimension and permit transluminal implantation. After the radially compressed mesh 10 is properly positioned at the implant site, a balloon catheter is preferably inserted into the prosthesis and the balloon is inflated until the prosthesis expands to the desired radial dimension. During balloon inflation the angled wire-ends exhibit a ratchet action by interlocking at each set of mesh openings as shown in FIG. 1(e). During balloon deflation the interlocked wire-ends remain latched in the maximum radial configuration which provides luminal support after the balloon catheter is withdrawn. The flexible mesh 10 preferably comprises a biocompatible or hypoallergenic metal or plastic, preferably stainless steel and the like.

Figure 2A:
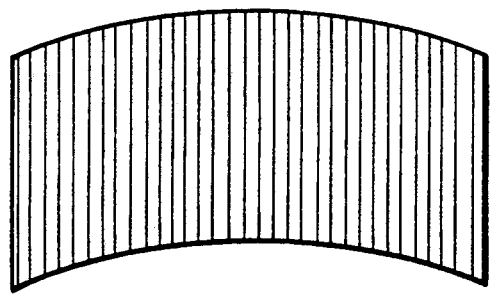
FIG. 2(a)-(f): describes an alternative implantable tubular prosthesis fabricated from a sheet of material which is folded back to create a longitudinal groove and free flap catch to permit selective ratcheting action.
Figure 2B:
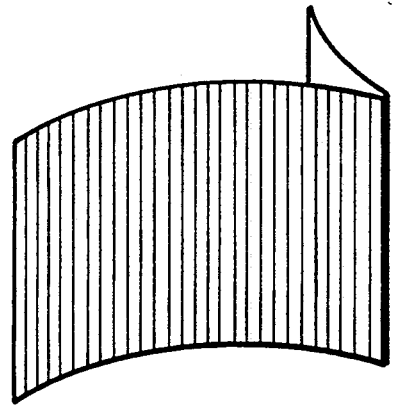
Figure 2C:
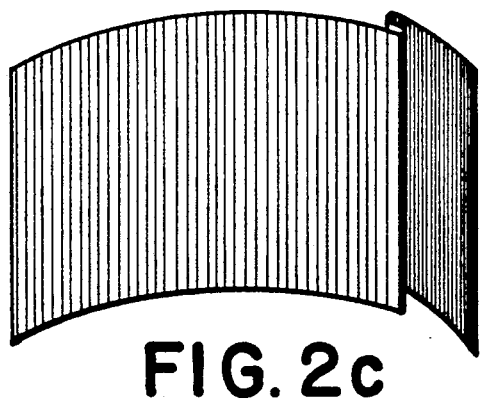
Figure 2D:
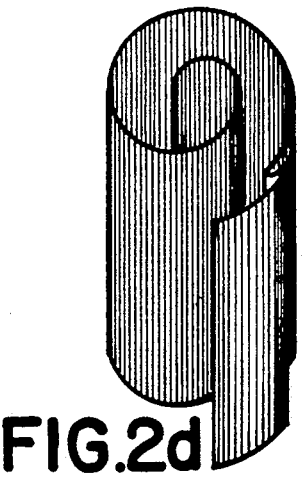
Figure 2E:
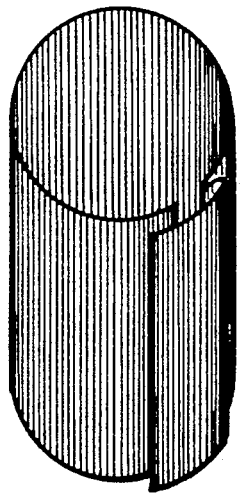
Figure 2F:
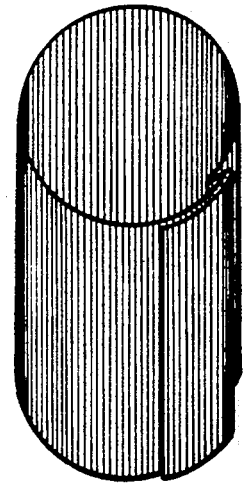

Referring now to FIGS. 2(a)-(f), there is shown another implantable tubular prosthesis embodiment comprising a sheet-like material 30 also made of a biocompatable or hypoallergenic metal or plastic. This implantable tubular prosthesis includes a resilient member comprising a sheet-like material and a ratcheting means including receiving means for receiving and locking a first of the transverse ends of the prosthesis. In FIG. 2(b) the sheet-like member 30 is folded back onto itself and preferably is bonded at the fold, e.g. by spot welding, adhesive, or heating. In FIG. 2(c) a second fold is added which forms a free flap "catch" 50 and longitudinal groove 60. This folded portion or groove is preferably disposed generally parallel to the first transverse end of the device. The groove 60 is designed to latch the free flap 40 which preferably has a tapered edge to facilitate latching. In addition, the edge 65 of the first fold of the longitudinal groove 60 can be oriented "downward" for facilitating the catching of the free flap 40. In FIG. 2(d) the sheet is rolled to reduce the radial dimension and permit transluminal implantation. After the rolled prosthesis is properly positioned at the implant site, a balloon catheter is inserted into the prosthesis lumen and inflated until the prosthesis radially expands to the catch position shown in FIG. 2(e). The balloon is then deflated and the prosthesis becomes latched in the expanded configuration shown in FIG. 2(f) as the free flap 40 locks into the longitudinal groove 60, or selective groove if a multiple groove embodiment is elected.

The implantable tubular prostheses described above are preferably designed to be removed after temporary service. Removal can also be accomplished with a standard endoscope by inserting a balloon catheter to dilate the prosthesis. After dilation, endoscopic forceps can be inserted to contract the prosthesis to a sufficiently small enough diameter for removal through the endoscope.

Although it is understood that the flexible mesh embodiment described herein is susceptible to endothelial migration, the sheet-like embodiment can be fabricated using a perfluorinated compound, such as polytetrafluorethylene coatings or materials. These embodiments will resist endothelial migration and may readily be removed from a body duct.

From the foregoing it can be realized that this invention provides improved implantable tubular prostheses for use as surgical stents and methods for their use. The prostheses possess multiple advantages which include large surface area for reducing tissue injury caused by high localized stresses, radial expansion by balloon catheters for generating greater expansive forces, and larger dilation ranges than precompressed spring devices. The invention also permits ratcheting of the prosthesis for selective radial expansion and locking at one or more selected diameters as the transverse ends of the prosthesis slide relative to one another. Although various embodiments have been illustrated, this was for the purpose of describing, but not limiting the invention. Various modifications, which will become apparent to one skilled in the art, are within the scope of this invention described in the attached claims.

I claim:

1. An implantable tubular prosthesis for insertion into a body duct comprising a mesh member comprising individual longitudinal and transverse wires bound together, said mesh member having longitudinal sides and transverse ends, a first of said transverse ends comprising a projecting portion comprising individual wires of said mesh member, said mesh member disposed in a generally tubular configuration whereby said individual wires of said projecting portion are disposed through said mesh member for fixing the diameter of said tubular prosthesis.

2. An implantable tubular prosthesis for insertion into a body duct comprising:
a resilient member having longitudinal sides and transverse ends, said resilient member disposed in a generally tubular configuration about a transverse axis, said resilient member comprising a flexible mesh comprising individual longitudinal and transverse wires bound together, said mesh having a plurality of openings therein, the mesh having a projecting portion for engaging with a select number of said openings to permit the selective radial expansion and locking of the tubular prosthesis in at least one fixed diameter.

3. The implantable tubular prosthesis of claim 2 wherein said projecting portion comprises extended portions of said individual wires of said flexible mesh.

4. The implantable tubular prosthesis of claim 3 wherein said extended portions of said individual wires are angularly disposed for engaging said select number of openings.

5. The implantable tubular prosthesis of claim 2 wherein said flexible mesh comprises biocompatible or hypoallergenic metal or plastic.

6. A method of implanting a tubular prosthesis into a body duct having an inner wall to be supported comprising:
(a) providing a resilient member having longitudinal sides and transverse ends, said resilient member disposed in a generally tubular configuration about a transverse axis, said resilient member comprising a flexible mesh comprising individual longitudinal and transverse wires bound together, said mesh having a plurality of openings therein, the mesh having a projecting portion for engaging with a select number of said openings to permit the selective radial expansion and locking of the tubular prosthesis in at least one fixed diameter;
(b) disposing said tubular prosthesis transluminally within said body duct;
(c) expanding said tubular prosthesis against the inner wall of said body duct; and
(d) locking said tubular prosthesis into a fixed diameter for supporting said inner wall of said body duct.

7. The method of claim 6 wherein said expanding step (c) comprises expanding said tubular prosthesis with a balloon catheter.

* * * * *